US00PP10563P

United States Patent [19]

Brandle et al.

[11] Patent Number: Plant 10,563

[45] Date of Patent: Aug. 18, 1998

[54] STEVIA PLANT NAMED 'RSIT 95-166-13'

[75] Inventors: James Brandle; Elizabeth Ann Sys; Albert Anthony Marsolais, all of Ontario, Canada

[73] Assignee: Royal-Sweet International Technologies Ltd. Part., Vancouver, Canada

[21] Appl. No.: 656,044

[22] Filed: May 29, 1996

[51] Int. Cl.[6] ..... A01N 5/00

[52] U.S. Cl. ..... Plt./100

[58] Field of Search ..... Plt./100

*Primary Examiner*—James R. Feyrer
*Assistant Examiner*—Kent L. Bell
*Attorney, Agent, or Firm*—Klarquist Sparkman Campbell Leigh & Whinston, LLP; Robert H. Barrigar; Alan E. Dow

[57] ABSTRACT

A novel *Stevia rebaudiana* Bertoni variety characterized by a high ratio of rebaudioside C to stevioside, a high ratio of rebaudioside C to rebaudioside A, and a high ratio of rebaudioside C to dulcoside A in its leaves.

2 Drawing Sheets

BACKGROUND OF THE INVENTION

The present invention relates to a new and distinct variety of stevia (*Stevia rebaudiana* Bertoni), referred to by the varietal name 'RSIT 95-166-13'.

Eight steviol glycosides with sweetening properties have been identified in leaf tissues of stevia. The four major glycosides are: stevioside, rebaudioside A, rebaudioside C, and dulcoside A. The chemical structures of these compounds are shown in FIG. 1. Each of these steviol glycosides has unique sensory properties, and they can be used singly or in combination to provide a sweetener that has sensory properties tailored to a specific use. Stevia sweeteners are non-caloric, making them suitable for diabetics and weight conscious consumers, and are pH-stable and heat-stable, making them useful in a wide range of bottled beverages, confectioneries, baked goods, and dairy and canned products. For reviews of the use of stevia as a source of sweeteners, see, e.g., Handro and Ferreira, 1989, Lee 1982, and Phillips, 1987.

We set out to develop stevia varieties with high concentrations of individual steviol glycosides that could be extracted and recombined in ratios suitable for specific product uses. Landrace stevia has a combination of steviol glycosides that is not optimal for all product applications.

We discovered our new variety in a cultivated area at the Agriculture and Agri-Food Canada Research Station near Delhi, Ontario, Canada ("Delhi Research Station"). The following unique combination of characteristics is outstanding in 'RSIT 95-166-13' and distinguishes it from its parents and all other stevia varieties of which we are aware: (1) a high ratio of rebaudioside C to stevioside; (2) a high ratio of rebaudioside C to rebaudioside A; and (3) a high ratio of rebaudioside C to dulcoside A.

This variety has not been observed under all possible environmental conditions. The following observations, measurements and comparisons describe plants grown under conditions that are similar to those generally used in commercial practice.

Asexual reproduction of this new variety by shoot-tip and stem cuttings was performed at the Delhi Research Station and showed that the foregoing characteristics are established and transmitted through succeeding asexual propagations.

BRIEF DESCRIPTION OF THE PHOTOGRAPHS

The accompanying photographs show typical specimens of this new variety, depicted in color as nearly true as is reasonably possible in a color photograph of this character. The photographs were taken at the Delhi Research Station in February 1996.

DETAILED DESCRIPTION

In the summer of 1994, ten plants from different seed germplasm accession of stevia from the People's Republic of China were grown for evaluation at the Delhi Research Station. Plant samples 'RSIT 94-1838', 'RSIT 94-1833', and 'RSIT 94-1560' were retained as a result of the higher than average concentrations of rebaudioside C on a dry weight basis in their leaves (Table 1). A plant ('RSIT 94-1829') selected from the variety 'Brazil Zairai' was also retained, since its leaves had higher than average rebaudioside C concentrations (Table 1). 'Brazil Zairai' is an open-pollinated landrace variety of stevia obtained from the Japanese National Germplasm Depository.

These four clones were used as parents and intercrossed in the fall and winter of 1994–1995. Half sib seeds were collected from clone, 'RSIT 94-1560' and were designated half sib population 'RSIT 95-166'. Plants from half sib population 'RSIT 95-166' were evaluated in the field in the summer of 1995 and one plant, 'RSIT 95-166-13', was selected on the basis of its novel steviol glycoside traits. See Brandle and Rosa (1992) for additional information regarding growth conditions and sexual crosses of Stevia varieties.

In trials conducted in 1994-95, the steviol glycoside profiles in leaves of the following stevia varieties were compared: 'RSIT 95-166-13'; 'RSIT 94-1560', the maternal parent used to produce the half sib population from which 'RSIT 95-166-13' was selected; 'RSIT 94-1838', 'RSIT 94-1833', and 'RSIT 94-1829', the paternal parents used to produce the half sib population from which RSIT 95-166-13 was selected; and 'Brazil'. In particular, the following were examined (on a dry weight basis): percent dulcoside A (% dulc.), percent stevioside (% stev.), percent rebaudioside C (% reb.C), percent rebaudioside A (% reb.A), and percent total glycosides (% total=% dulc.+% stev.+% reb.C+% reb.A). The results of the comparison are shown in Table 1.

'RSIT 95-16613' was dug out of the field in the fall of 1995 and vegetatively propagated at the Delhi Research Station by shoot-tip and stem cuttings.

TABLE 1

Steviol Glycoside Profiles of 'RSIT 95-166013', 'RSIT 94-1560', 'RSIT 94-1838', 'RSIT 94-1833', 'RSIT 94-1829', and 'Brazil'

| Variety | Year | % dulc. | % stev. | % reb. C | % reb. A | % Total |
|---|---|---|---|---|---|---|
| 95-166-13 | 1995a[1] | 0.47 | 0.30 | 14.40 | 0.37 | 15.55 |
| 95-166-13 | 1995b[2] | 0.82 | 0.36 | 14.78 | 0.44 | 16.41 |
| 94-1560 | 1995 | 0.64 | 3.78 | 5.59 | 3.70 | 13.71 |
| 94-1560 | 1994 | 0.91 | 4.9 | 7.2 | 4.9 | 17.91 |
| 94-1838 | 1994 | 0.96 | 4.4 | 10.0 | 5.7 | 21.06 |
| 94-1833 | 1994 | 1.19 | 4.8 | 7.4 | 4.3 | 17.69 |
| 91-1829 | 1994 | 1.75 | 7.2 | 6.9 | 4.6 | 20.45 |
| Brazil | 1995 | 0.25 | 7.61 | 0.54 | 3.00 | 11.40 |

[1]1995a was sampled in August 1995.
[2]1995b was sampled in September 1995.

Taxonomic Description of 'RSIT 95-166-13'

Figure 2:
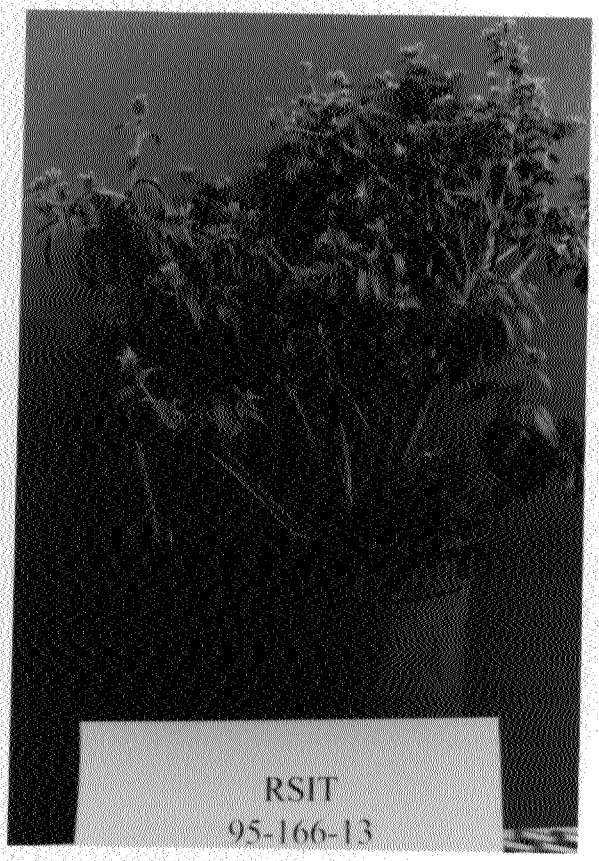
FIG. 2 is a view of a plant of the present invention.
Figure 3:
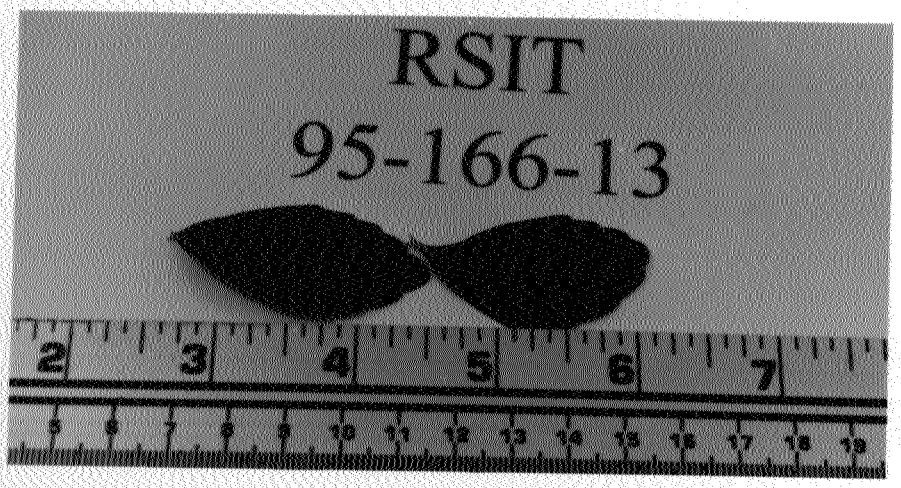
FIG. 3 is an enlarged view of leaves of the plant of FIG. 2.

'RSIT 95-166-13' is a suffrutescent, erect perennial (FIG. 2). Field-grown plants may attain a height of 1.1 meters, but more commonly have a height of 6–8 dm. The stems are round, pubescent, and have internodes of medium length. The leaves are simple, opposite, sessile, exstipulate, and oblanceolate. The leaf apices are obtuse and the leaf margins are crenate above the middle and entire on a cuneately narrow base. The leaves are three-nerved and conspicuously veiny. The leaf surface is puberulent with short glandless hairs. The largest cauline leaves are up to 7 cm long and 3 cm wide and are often proliferous in the axils (FIG. 3).

The inflorescence is loosely paniculate with the heads appearing opposite the bracts in irregular sympodial cymes. The flower corollas have a pale purple throat and white limb. The seed are nearly uniform achenes, 15–17 aristate (Robinson, 1930).

Method of Determining Steviol Glycosides and Concentrations

Fresh leaf samples were harvested from field-grown stevia plants and stored in a freezer prior to extraction. Samples were freeze dried, ground to pass through a 40-mesh screen, and again freeze dried before extraction. Ground, freeze-dried plant material (300 mg.) was weighed into a 15 ml (polypropylene centrifuge tube (Fisher). Ten ml of 1:1 (v/v) acetonitrile-water (acetonitrile from Caledon Laboratories Ltd., Georgetown, Ontario, 190 HPLC grade) was added to each sample. Sample tubes were suspended in an ultrasonic bath (Lab-line Inst. model #9333, Melrose Park, IL) at maximum ultrasonication (#9) for 15 min with occasional stirring and rotation to ensure optimal extraction. Sample tubes were transferred to a centrifuge (International Centrifuge, Model V Size 2, International Equipment, Boston, MA) and centrifuged at 1500 rpm for 15 min. The extraction solvent was transferred to a volumetric flask with a Pasteur pipette. For routine analyses, duplicate extractions were utilized and the solvent transferred to a 25 ml volumetric flask filled to volume with acetonitrile. Samples were filtered through a 0.45 micron filter (Acrodisc 13, Gelman Sciences, Ann Arbor, MI).

Analyses were performed on a liquid chromatograph (Hewlett-Packard 1090) equipped with a three-channel solvent delivery system, auto sampler, and diode array detector interfaced with a chem station. Stevioside, rebaudioside A, rebaudioside C, and dulcoside A standards were supplied by FWB Chemical Consulting Ltd., Calgary, Alberta, Canada. Stevioside was also obtained from Sigma Chemical Co., St. Louis, Mo. Due to the wide variation in plant material analyzed, co-eluting peaks occasionally were apparent in the chromatogram. Often these plant constituents were eliminated by filtering them through a Waters NH2 Sep-Pak cartridge (Part No. WATO 20535) prior to analysis. For routine analyses, only stevioside was used as a standard. The response factor found for stevioside was used for the other three steviol glycosides after correcting for differences in molecular weight. In order to monitor this assumption during the sample determinations, a standard sample of rebaudioside A was analyzed after each calibration.

The chromatographic column was a Waters cartridge carbohydrate column (Part No. WAT 044355) having an inside diameter of 250×4.6 mm. The guard column was a carbohydrate sentry guard column (Part No. WAT 046895). The "A" solvent was $H_2O$ (pH 5.25 with AcOH), the "B" solvent was acetonitrile, and the "C" solvent was acetonitrile. The flow rate was 1.5 ml/min. The time table for use of solvents A, B, and C is found in Table 2.

TABLE 2

Time table for use of Solvent A ($H_2O$, pH 5.25 with AcOH), Solvent B (acetonitrile), and Solvent C (acetonitrile)

| Time (min.) | % Solvent A | % Solvent B | % Solvent C |
|---|---|---|---|
| 0 | 13 | 43 | 44 |
| 12 | 17.5 | 41 | 41.5 |
| 26 | 24 | 38 | 39 |
| 26.1 | 13 | 43 | 44 |

The post time was six minutes and the elution times for the steviol glycosides were 14.5 minutes for dulcoside A, 18.8 minutes for stevioside, 20.4 minutes for rebaudioside C, and 23.5 minutes for rebaudioside A. Retention times of the components of interest decreased with extensive use of the column. It was usually sufficient to simply reduce the amount of water in the initial chromatographic conditions to restore the retention times. Individual columns have been used for more than one thousand samples. Guard columns typically were replaced after about 300 samples or when system pressure became excessive. Periodically the column was washed with water to remove other plant constituents which accumulated on the column. Steviol glycosides were identified by retention time and concentrations were determined by an external standards method.

Steviol glycosides may be produced from leaves or other parts of 'RSIT 95-166-13' and formulated into a sweetener for use in the food industry or by consumers by any conventional method. See, e.g., U.S. Pat. No. 4,892,938. Purified extract solutions may be directly added to a foodstuff or beverage, for example, in liquid form or converted to a crystalline form. The sweetness intensity of steviol glycosides is usually about 150 to 300 times that of sucrose, depending on the concentration of the steviol glycosides used. If desired, stevia extracts can be suitably diluted with a conventional diluent, e.g., a tasteless soluble starch, to achieve a sweetness intensity comparable to that of sugar (i.e., sucrose). For convenient use by the consumer, a unit of a stevia sweetener, e.g., an amount having a total sweetness approximately that of a standard lump of sugar, can be packaged for commercial distribution in small paper bags or in other forms known in the art. Steviol glycosides from 'RSIT 95-166-13' can be used singly or in combination with steviol glycosides from other stevia varieties or with other conventional sweeteners to provide a sweetener composition hat has sensory properties tailored to a specific use.

All publications and published patent documents cited in his specification are incorporated herein by reference to the ame extent as if each individual publication or patent pplication was specifically and individually indicated to be ncorporated by reference.

Reference Cited

Brandle, J., Rosa, N. (1992). "Heritability for Yield, Leaf: Stem Ratio and Stevioside Content Estimated from a Landrace Cultivar of *Stevia rebaudiana.*" *Can. J. Plant Sci.* 72: 1263-1266.

Handro, W., Ferreira, C.M. (1989). "Stevia rebaudiana (Bert.) Bertoni: Production of Natural Sweeteners." In: *Biotechnology in Agriculture and Forestry,* vol. 7, Medicinal and Aromatic Plants II (ed. Y.P.S. Bajaj), Springer Verlag, Berlin, Heidelberg, pp. 468-487.

Lee, J.I., et al. (1982). "New High Rebaudioside-A Stevia Variety 'Suweon 11'." Res. Rept. ORD 24(C):186–188.

Phillips, K.C. (1987). "Stevia: Steps in Developing a New Sweetener." In: *Developments in Sweeteners*-3, Elsevier Applied Science, London (ed: T.H. Grenby). pp. 1–43.

Robinson, R.L. (1930). *Contributions from the Gray Herbarium of Harvard University XC,* The Gray Herbarium of Harvard University, Cambridge, Mass. pp. 78–91.

U.S. Pat. No. 4,892,938 (1990).

We claim:

1. A new and distinctive variety of *Stevia rebaudiana* Bertoni plant, substantially as herein shown and described.

* * * * *

STRUCTURES

| | $R_1$ |
|---|---|
| Stevioside | glc $^{2}$-glc |
| Rebaudioside A | glc $^{2,3}$<sup></sup>glc |
| Rebaudioside C | glc $^{2,3}$<sup></sup>glc |
| Dulcoside A | glc $^{2}$-rham |

glc ; glucose
rham ; rhamnose

UNITED STATES PATENT AND TRADEMARK OFFICE
CERTIFICATE OF CORRECTION

PATENT NO. : Plant 10,563

DATED : August 18, 1998

INVENTOR(S) : James Brandle; Elizabeth Ann Sys; Albert Anthony Marsolais

It is certified that error appears in the above-identified patent and that said Letters Patent is hereby corrected as shown below:

Column 3, line 6 change "'RSIT 95-166013'" to read --'RSIT 95-166-13'--.

Column 3, line 47 change "15 ml (polypropylene" to read --15 ml polypropylene--.

Figure 1:
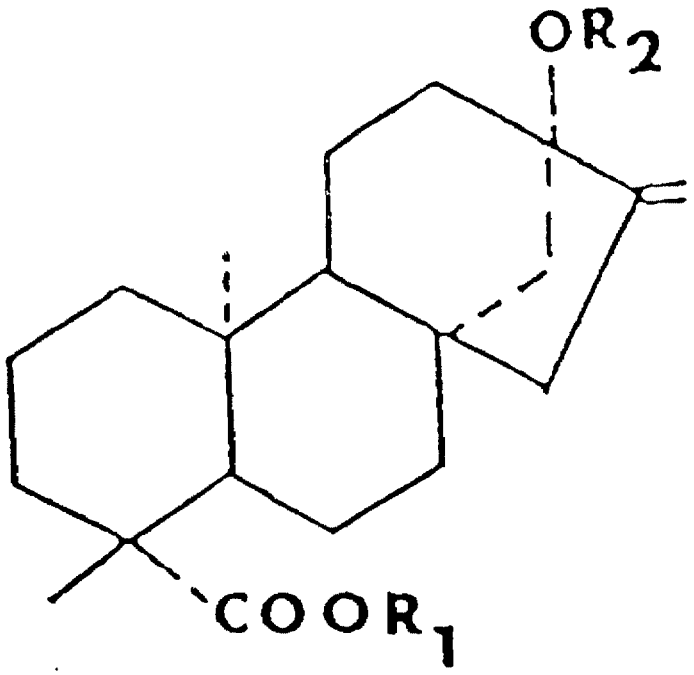
FIG. 1 shows the chemical structure of four major steviol glycoside sweeteners in stevia, stevioside, rebaudioside A, rebaudioside C, and dulcoside A.

In the Drawings:

Fig. 1, is amended to appear as attached.

Signed and Sealed this

Eleventh Day of April, 2000

*Attest:*

*Attesting Officer*

Q. TODD DICKINSON

*Director of Patents and Trademarks*

UNITED STATES PATENT AND TRADEMARK OFFICE

CERTIFICATE OF CORRECTION

PATENT NO. : Plant 10,563

DATED : August 18, 1998

INVENTOR(S) : James Brandle; Elizabeth Ann Sys; Albert Anthony Marsolais

It is certified that error appears in the above-identified patent and that said Letters Patent is hereby corrected as shown below:

STRUCTURES

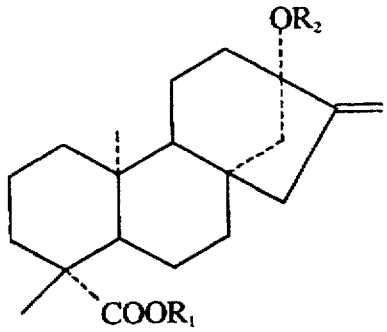

| | $R_1$ | $R_2$ |
|---|---|---|
| Stevioside | glc $^{2}$–glc | glc |
| Rebaudioside A | glc $^{2}$–glc, $^{3}$–glc | glc |
| Rebaudioside C | glc $^{2}$–rham, $^{3}$–glc | glc |
| Dulcoside A | glc $^{2}$–rham | glc |

glc ; glucose
rham ; rhamnose

FIG. 1